United States Patent [19]

Saville

[11] Patent Number: Plant 5,450

[45] Date of Patent: Apr. 30, 1985

[54] ROSE PLANT—SAVASPIR

[75] Inventor: F. Harmon Saville, Rowley, Mass.

[73] Assignee: Nor'East Miniature Roses, Inc., Rowley, Mass.

[21] Appl. No.: 535,737

[22] Filed: Sep. 26, 1983

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety of bright currant red coloring long lasting on the plant and as a cut flower.

1 Drawing Figure

The present invention relates to a new and distinct variety of rose plant of the miniature rose class, which was originated by my crossing as seed parent the rose known as "Sheri Anne" (U.S. Plant Pat. No. 3,826) and the rose known as "Tamango" (U.S. Plant Pat. No. 2,857) as pollen parent. The varietal denomination of this new variety is "Savaspir".

Among the novel characteristics possessed by this new variety which distinguish it from its parents and all other varieties of which I am aware are its bright currant red flowers of exhibition form with good to heavy petalage which are long lasting on the plant and as cut flowers. Asexual reproduction by budding of the new variety as performed in Essex County, Mass., shows that the foregoing and other distinguishing characteristics come true to form and are established and transmitted through succeeding propagations.

The accompanying drawings show typical specimens of the vegatative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "46A" is plate 46A of The Royal Horticultural Society Colour Chart.

Parentage: Seedling.
*Seed parent.*—"Sheri Anne".
*Pollen parent.*—"Tamango".
Class: Miniature.

The following observations are made of specimens grown outdoors in Essex County, Mass., during the month of July.

FLOWER

Blooming habit: Recurrent, near continuous.
Bud:
(1) *Size.*—Medium.
(2) *Form.*—Ovate, short, becoming urn shaped as petals unfurl.
(3) *Color.*—When sepals first divide — currant red near 46A. When petals begin to unfurl — near 46A to 46 B.
(4) *Sepals.*—Smooth, longer than bud.

(5) *Peduncle.*—Length — $\frac{3}{4}$ to $1\frac{1}{4}$ inches. Aspect — straight. Strength — erect. Color — near 144B.

Bloom:
(1) *Size.*—Average size when fully expanded — about $1\frac{3}{8}$ to $1\frac{1}{2}$ inches.
(2) *Borne.*—Singly and sprays.
(3) *Form.*—High centered at first, becoming flat, petals reflex upon opening; flower maintains symmetrical exhibition form.
(4) *Petalage.*—Number of petals under normal conditions — about 26 to 40.
(5) *Color.*—As currant red buds 46A unfurl color remains stable between 46A to 46B with petals underside surface slightly lighter 46C. Color holds upon aging.

Petals:
(1) *Texture.*—Thick.
(2) *Appearance.*—Inside — velvety, outside — satiny.
(3) *Form.*—Oval.
(4) *Arrangement.*—Regularly arranged, shingle-like.
(5) *Petaloids in center.*—Few.
(6) *Persistence.*—Drop off cleanly.
(7) *Fragrance.*—Slight.
(8) *Lasting quality.*—Very long lasting on plant and as cut flower.

REPRODUCTIVE ORGANS

Stamens, filaments and anthers:
(1) *Arrangement.*—Regularly arranged around styles.
(2) *Color.*—Near 14C.

Pollen:
*Color.*—Near 14B.

Styles: Even length, long.

Stigmas:
*Color.*—Near 39C.

Hips:
*Shape.*—Globular.
*Size.*—About $\frac{5}{8}$ inch.
*Color.*—Orange red.
*Do seeds protrude?*—No.

PLANT

Form: Upright.
Growth: Very vigorous.
*Height attained.*—About 12 to 18 inches.
Foliage: Compound 5 to 7 leaflets.
(1) *Size.*—Medium.

(2) *Quantity.*—Abundant.

(3) *Color.*—New foliage: Upper side — near to 176A. Under side — near to 185C. Old foliage: Upper side — near 137A. Under side — near 137D.

(4) *Shape.*—Oval.

(5) *Texture.*—Upper side is slightly glossy and under side is dull.

(6) *Edge.*—Serrated.

(7) *Serration.*—Serrulate.

(8) *Leaf stem.*—Color — near to 143A. Under side — near 143C.

(9) *Stipules.*—Medium.

(10) *Resistance to disease.*—Blackspot — average. Mildew — average. Rust — average.

Wood:

(1) *New wood.*—Color — near 145A. Bark — Smooth.

(2) *Old wood.*—Color — near 143A. Bark — smooth.

Thorns:

(1) *Thorns.*—Quantity (main stalk): ordinary. On laterals from stalk — few. Form —long, straight, thin, pointed, angled slightly downward. Length — medium. Color — near 180D. Position — irregular.

(2) *Prickles.*—Few.

Winter hardiness: Requires ordinary protection in extreme climates.

I claim:

1. A new and distinct variety of rose plant of the miniature rose class, substantially as shown and described, characterized particularly by bright currant red flowers of good exhibition form and medium to heavy petalage with petals reflexing upon opening while retaining good form and flowers which are very long lasting on the plant and after cutting.

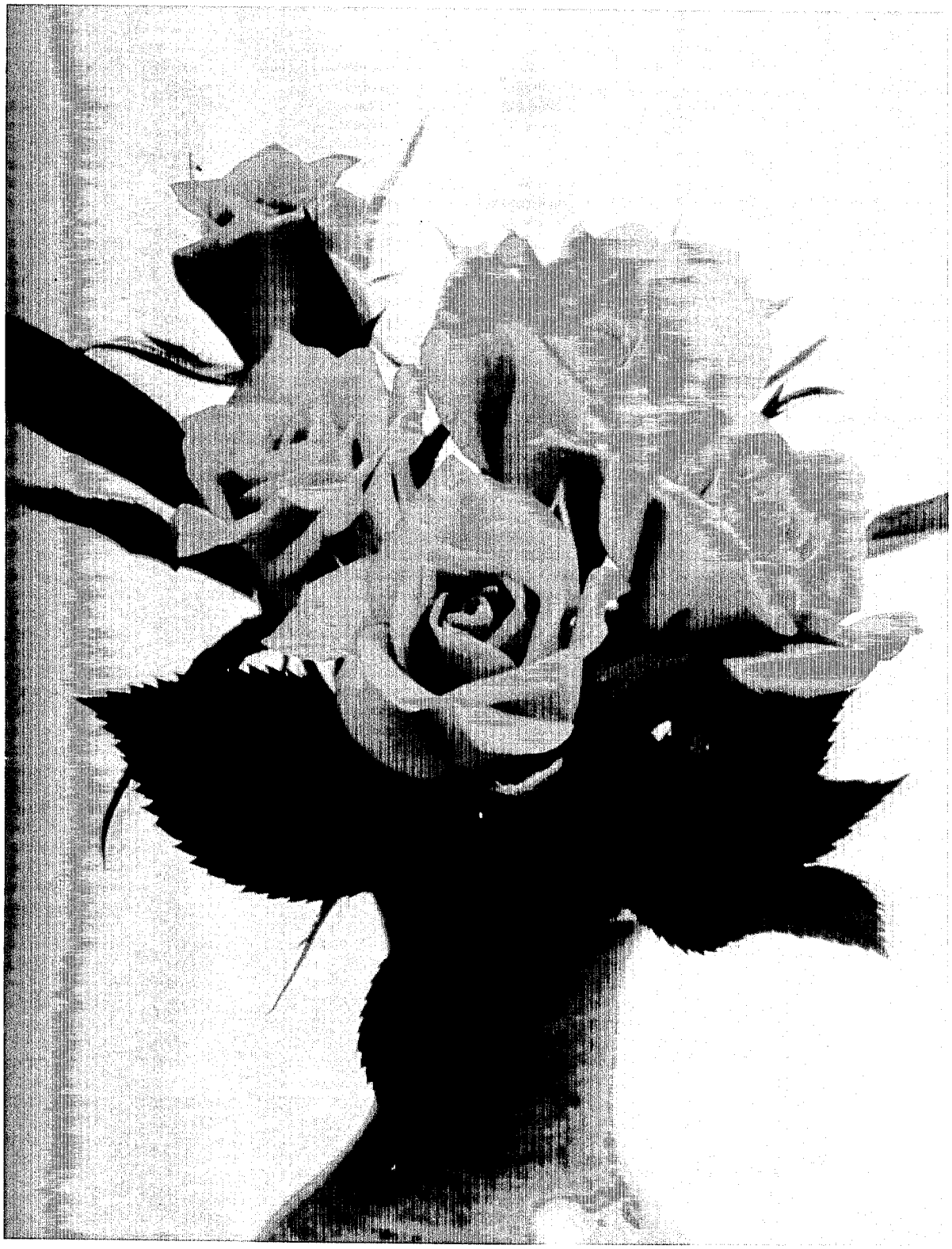

* * * * *